US008426215B2

(12) United States Patent
Mueller et al.

(10) Patent No.: US 8,426,215 B2
(45) Date of Patent: Apr. 23, 2013

(54) GAS CHROMATOGRAPH AND METHOD FOR ANALYZING A MIXTURE OF SUBSTANCES BY GAS CHROMATOGRAPHY

(75) Inventors: Friedhelm Mueller, Linkenheim-Hochstetten (DE); Udo Gellert, Bellheim (DE)

(73) Assignee: Siemens Aktiengesellschaft, Munich (DE)

( * ) Notice: Subject to any disclaimer, the term of this patent is extended or adjusted under 35 U.S.C. 154(b) by 1281 days.

(21) Appl. No.: 10/950,395

(22) Filed: Sep. 28, 2004

(65) Prior Publication Data
US 2005/0123452 A1 Jun. 9, 2005

Related U.S. Application Data

(63) Continuation of application No. PCT/DE03/01040, filed on Mar. 28, 2003.

(30) Foreign Application Priority Data

Mar. 28, 2002 (DE) .................................. 102 14 211
Sep. 25, 2002 (DE) .................................. 102 44 601

(51) Int. Cl.
*G01N 30/02* (2006.01)

(52) U.S. Cl.
USPC ......... 436/161; 436/139; 73/23.31; 73/23.38; 95/86

(58) Field of Classification Search .................... 422/83, 422/88–91; 96/104, 105, 101–103, 106; 73/23.22, 23.4, 23.42, 23.31; 436/161, 106, 436/133, 139–141; 95/82, 86, 87
See application file for complete search history.

(56) References Cited

U.S. PATENT DOCUMENTS

| 3,236,603 | A | * | 2/1966 | Durrett et al. ................... 422/89 |
| 3,683,671 | A | * | 8/1972 | Van Swaay .................. 73/25.03 |

(Continued)

FOREIGN PATENT DOCUMENTS

| DE | 28 40 612 A1 | 3/1980 |
| DE | 198 08 213 A1 | 9/1999 |

(Continued)

OTHER PUBLICATIONS

Ji, Zhenghua et al., Porous layer open-tubular capillary columns: preparations, applications and future directions, May 21, 1999, J. Chromatography A, 842(1-2), pp. 115-142.*

(Continued)

*Primary Examiner* — Jan Ludlow
(74) *Attorney, Agent, or Firm* — Staas & Halsey LLP

(57) ABSTRACT

A gas chromatograph for analyzing natural gas, with a first separation column (6). A first detector (7) is provided following the first separation column, the first separation column and the first detector operable to separate or detect propane and higher hydrocarbons. A second separation column (8) and a second detector (9) following it are provided to separate or detect carbon dioxide and ethane. A third separation column (10) and a third detector (11) following it are provided to separate or detect nitrogen and methane. A controllable changeover device (12) is provided between the second separation column (8) and the third separation column (10) to discharge eluates following methane. The first, second and third separation columns (6, 8, 10) and the first, second and third detectors (7, 9, 11) are connected in series. At least the first and the second detectors (7, 9) are operable to detect a mixture of substances flowing through them in a non-destructive manner.

15 Claims, 1 Drawing Sheet

U.S. PATENT DOCUMENTS 4,650,499 A * 3/1987 Scott .................................. 95/82
2001/0029772 A1 10/2001 Binz et al.

FOREIGN PATENT DOCUMENTS

| | | |
|---|---|---|
| DE | 101 05 728 A1 | 9/2002 |
| EP | 0 406 757 A2 | 1/1991 |
| EP | 1061365 A1 * | 12/2000 |
| WO | WO 02/50530 A2 | 6/2002 |

OTHER PUBLICATIONS

Noij, Th. et al., Trace analysis of halogenated hydrocarbons in gaseous samples by capillary gas chromatography, Dec. 1988, Chromatographia, 26(1), pp. 149-156.*

Drews, A.W. (1998). Manual on Hydrocarbon Analysis (6th Edition): (MNL 3). (pp. 287-301). ASTM International. Online version available at: http://www.knovel.com/web/portal/browse/display?_EXT_KNOVEL_DISPLAY_bookid=1740&VerticalID=0.*

* cited by examiner

GAS CHROMATOGRAPH AND METHOD FOR ANALYZING A MIXTURE OF SUBSTANCES BY GAS CHROMATOGRAPHY

This is a Continuation of International Application PCT/DE03/01040, with an international filing date of Mar. 28, 2003, which was published under PCT Article 21(2) in German, and the disclosure of which is incorporated into this application by reference.

FIELD AND BACKGROUND OF THE INVENTION

Natural gas is primarily composed of methane and other gaseous hydrocarbons, such as ethane, butane, propane, etc. Furthermore, it also contains nitrogen and carbon dioxide. The composition of natural gas depends on where it originates from. The exact analytical determination of the composition is done by gas chromatography. Partial analyses are frequently performed, which are subsequently combined to obtain an overall result.

OBJECTS OF THE INVENTION

One object of the invention is to analyze natural gas using a single separation column combination, i.e., a single scheme of analysis.

SUMMARY OF THE INVENTION

Objects of the invention are achieved by a gas chromatograph for analyzing natural gas having a first separation column. A first detector is provided following the first separation column, the first separation column and the first detector operable to separate or detect propane and higher hydrocarbons. A second separation column and a second detector following it are provided to separate or detect carbon dioxide and ethane. A third separation column and a third detector following it are provided to separate or detect nitrogen and methane. A controllable changeover device is provided between the second separation column and the third separation column to discharge eluates following methane. The first, second and third separation columns and the first, second and third detectors are connected in series. At least the first and the second detectors are operable to detect a mixture of substances flowing through them in a non-destructive manner.

The separation column combination according to the invention can be used to determine the composition of natural gas using a single scheme of analysis, such that cycle times of less than 5 minutes can be achieved. With the discharge of the eluates following methane, these eluates are kept away from the third separation column, which is specially configured for the separation of nitrogen and methane and if required oxygen and carbon monoxide and from which subsequent eluates reaching this column can be removed only with considerable effort.

To be able to detect even longer-chain hydrocarbons than, for example, n-hexane without requiring excessive retention times, it is advantageously provided that after detection of a specified higher, i.e., longer-chain hydrocarbon, in this case, e.g., n-hexane by means of the first detector, the first and second separation columns can be back-flushed with carrier gas via the controllable changeover device and that an additional detector is arranged in front of the first separation column to detect eluates following the specified higher hydrocarbon.

A separation column combination found to be particularly advantageous is one in which the first separation column is a WCOT (Wall Coated Open Tubular) column with non-polar stationary phase, the second separation column is a PLOT (Porous Layer Open Tubular) column with a non-polar stationary phase and the third separation column is a PLOT column with molecular sieve, particularly a 5 angstrom molecular sieve. The diameter of the separation columns is preferably 0.25 mm.

For the detectors, each of which is located in front of the corresponding separation column, only those come into consideration which do not destroy the mixture of substances, i.e., for example, a suitable thermal conductivity detector, an optical detector or a detector working with acoustic surface waves. To prevent the separation efficiency of the separation column combination from being affected, the measurement paths of the corresponding detectors through which the mixture of substances flows are preferably configured such that their cross-sectional dimensions at least approximately correspond to those of the separation columns. As a result, the dosing plug, which should be as short and sharply delimited as possible and through which the mixture of substances is introduced into the separation column combination, is not disturbed at the detector sites and any reversal of the previously achieved separation and any further separations are prevented.

According to a preferred embodiment of the gas chromatograph according to the invention, at least the detectors located in front of the separation columns each consist of a thermal conductivity detector with heating resistors disposed in a bridge circuit, of which two diagonally opposite heating resistors in the two different halves of the bridge are arranged in the measurement path. The other two heating resistors are located in a reference path through which carrier gas flows.

BRIEF DESCRIPTION OF THE DRAWINGS

The invention will now be described in greater detail with reference to the drawing figures in which.

DETAILED DESCRIPTION OF PREFERRED EMBODIMENTS

Figure 1:
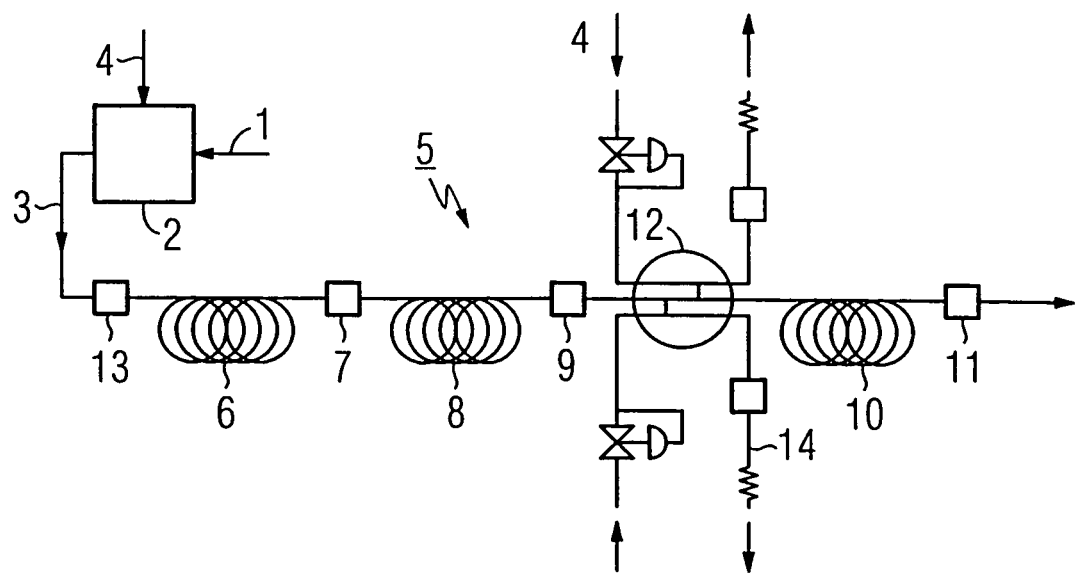
FIG. 1 shows an exemplary embodiment of the gas chromatograph according to the invention.

FIG. 1 shows a gas chromatograph for analyzing a natural gas sample 1. The natural gas, which has been removed from a different technical process and treatment, is supplied to a dosing unit 2. The dosing unit 2 is used to inject a specified dose of the natural gas sample 1 as a short and sharply delimited dosing plug 3 into a carrier gas stream 4 at a predefined instant. The dose and the carrier gas are supplied it to a separation column combination 5 in which the natural gas components contained in the sample plug 3 are separated and sequentially detected and quantitatively identified.

The separation column combination 5 consists of a first separation column 6 followed by a first detector 7, a second separation column 8 followed by a second detector 9 and a third separation column 10 followed by a third detector 11. The separation columns 6, 8, 10 and the detectors 7, 9, 11 are arranged in line in a series connection. A controllable changeover device 12 is arranged between the second separation column 8 and the third separation column 10, in this case after the second detector 9. An additional detector 13 is disposed in front of the first separation column 6.

The first separation column 6 is configured as a WCOT column with non-polar stationary phase, e.g., CP Sil 5 CB, for separating propane and higher hydrocarbons, such as propane, butane, pentane and hexane, which are detected by the first detector 7.

The second separation column 8 is configured as a PLOT column (thin film column) with non-polar stationary phase, e.g., PoraPLOT Q, for separating carbon dioxide and ethane, which are detected by the second detector 9.

The third separation column 10 is configured as a PLOT column with a molecular sieve, to separate nitrogen, methane and if required oxygen and carbon monoxide, which are detected by the third detector 11. Particularly, the molecular sieve is a 5 angstrom molecular sieve as a separation phase (molecular sieve column).

Other natural gas components must be prevented from reaching the molecular sieve column 10 because they can only be removed by conditioning the molecular sieve column 10. For this reason, the eluates following methane, i.e., carbon dioxide, ethane, propane, etc., after they exit from the separation column 8, are discharged via a gas path 14 by means of the controllable changeover device 12. The changeover device 12 can be controlled as a function of the presence of carbon dioxide at the second detector 9 or a specified period following the detection of methane by the second detector 9.

After n-hexane has been detected by the first detector 7, the first and second separation columns 6, 8 are back-flushed with the carrier gas 4 via the controllable changeover device 12, such that all longer-chain hydrocarbons that elute after n-hexane are removed from the separation column combination 5 and detected by the additional detector 13.

Figure 2:
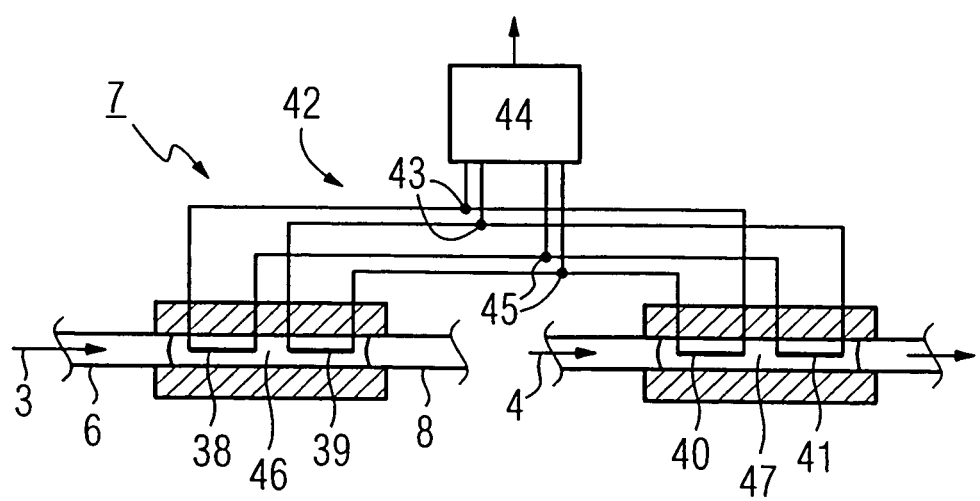
FIG. 2 shows an exemplary embodiment of a detector.

FIG. 2 shows an example of one of the detectors 7, 9, 13 and possibly 11. The detectors are arranged in the line with the separation column combination 5 such that the mixture of substances flows through them unhindered. The detector 7, shown here by way of example, is configured as a thermal conductivity detector and has four wire-shaped heating resistors 38, 39, 40 and 41 arranged in a bridge circuit 42. The bridge circuit 42 is supplied with a current from a detector circuit 44 at two opposite circuit points 43, and the voltage that occurs between the two other opposite circuit points 45 is detected by the detector circuit 44 to generate a detector signal.

The heating resistors 38 and 39, which are diagonally opposite each other in the bridge circuit 42, are arranged in a measurement path 46 of the detector 7, while the two other two heating resistors 40 and 41 are disposed in a reference path 47. The thermal conductivity detector 7 with its measurement path 46 is located between the separation columns 6 and 8, while the carrier gas 4 flows through the reference path 47. The reference path 47 can be used as the measurement path and the measurement path 46 as a reference path of another detector as long as the carrier gas 4 flows through one of the two paths 46 and 47, while the mixture of substances flows through the other measurement path. The measurement path 46 and possibly the reference path 47 are configured such that their cross-sectional inside dimensions correspond to those of the connected separation columns 6 and 8, so that the separation state of the more or less separated mixture of substances flowing through them is not disturbed.

The above description of preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A gas chromatographic method for analyzing natural gas, comprising:
   conducting the gas sequentially through a first separation column followed by a first detector, a second separation column followed by a second detector and a third separation column followed by a third detector, the first, second and third separation columns being connected in sequential order in series;
   separating and detecting, in the first separation column and detector, propane and higher hydrocarbons in a non-destructive manner;
   separating and detecting, in the second separation column and detector, carbon dioxide and ethane in a non-destructive manner;
   separating and detecting, in the third separation column and detector, nitrogen and methane; and
   discharging, by means of a controllable changeover device provided between the second detector and the third separation column, eluates following methane, thereby preventing the eluates from reaching the third separation column.

2. The gas chromatographic method of claim 1, wherein the third separation column and the third detector additionally separate or detect oxygen and carbon monoxide.

3. The gas chromatographic method of claim 1, wherein, after a specified higher hydrocarbon has been detected by the first detector, the first and second separation columns are back-flushed with carrier gas via the controllable changeover device.

4. The gas chromatographic method of claim 3, wherein the specified hydrocarbon is n-heptane.

5. The gas chromatographic method of claim 3, further comprising detecting, using an additional detector, eluates following the specified higher hydrocarbon prior to the first separation column.

6. The gas chromatographic method of claim 5, wherein at least the additional detector has a measurement path and a cross-sectional dimension approximately corresponding to those of the separation columns.

7. The gas chromatographic method of claim 6, wherein the additional detector is a thermal conductivity detector.

8. The gas chromatographic method of claim 1, wherein, the first separation column is a wall coated open tubular column with non-polar stationary phase.

9. The gas chromatographic method of claim 1, wherein, the second separation column is a porous layer open tubular column with a non-polar stationary phase.

10. The gas chromatographic method of claim 1, wherein, the third separation column is a porous layer open tubular column with molecular sieve.

11. The gas chromatographic method of claim 10, wherein the molecular sieve is a 5 angstrom molecular sieve.

12. The gas chromatographic method of claim 1, wherein at least the first and the second detectors have a measurement path and the cross-sectional dimensions of the measurement paths approximately correspond to cross-sectional dimensions of the separation columns.

13. The gas chromatographic method of claim 12, wherein at least one of the detectors is a thermal conductivity detector.

14. The gas chromatographic method of claim 13, where said at least one of the detectors has heating resistors arranged in a bridge circuit, a first two of the heating resistors being located diagonally opposite each other in two different bridge halves of the bridge circuit and the first two heating resistors being disposed in the measurement path.

15. The gas chromatographic method of claim 14, wherein a second two of the heating resistors are disposed in a reference path.

* * * * *